United States Patent [19]
Grill, Jr. et al.

[11] Patent Number: 5,324,322
[45] Date of Patent: Jun. 28, 1994

[54] THIN FILM IMPLANTABLE ELECTRODE AND METHOD OF MANUFACTURE

[75] Inventors: Warren M. Grill, Jr.; Graham H. Creasey, both of Cleveland Hts., Ohio; David A. Ksienski, Hermosa Beach, Calif.; Claude S. Veraart, Brussels, Belgium; J. Thomas Mortimer, Chagrin Falls, Ohio

[73] Assignee: Case Western Reserve University, Cleveland, Ohio

[21] Appl. No.: 871,352

[22] Filed: Apr. 20, 1992

[51] Int. Cl.⁵ .............................................. A61N 1/04
[52] U.S. Cl. ................................. 607/118; 128/642
[58] Field of Search ........ 128/639, 642, 644, 783-786, 128/804; 607/118

[56] References Cited

U.S. PATENT DOCUMENTS

| | | | |
|---|---|---|---|
| 4,133,735 | 1/1979 | Afromowitz et al. | 128/642 |
| 4,602,624 | 7/1986 | Naples et al. | 128/784 |
| 4,677,989 | 7/1987 | Robblee | 128/784 |
| 4,717,581 | 1/1988 | Robblee | 427/2 |
| 4,743,493 | 5/1988 | Sioshansi et al. | 428/217 |
| 4,837,049 | 6/1989 | Byers et al. | 128/642 |
| 4,903,702 | 2/1990 | Putz | 128/642 |
| 5,074,313 | 12/1991 | Dahl et al. | 128/786 |

FOREIGN PATENT DOCUMENTS 2195897  4/1988  United Kingdom ............... 128/642

Primary Examiner—Stephen C. Pellegrino
Assistant Examiner—M. Peffley
Attorney, Agent, or Firm—Fay, Sharpe, Beall, Fagan, Minnich & McKee

[57] ABSTRACT

A sheet (30) of polymeric material defines a cuff portion (A), a contact portion (B), and an interconnecting elongated lead portion (C). Using physical vapor deposition (PVD), chemical vapor deposition (CVD), or other thin film deposition techniques, a plurality of electrodes (12), contact pads (16), and interconnecting leads (14) are deposited on the base layer. An elastomer covering layer (18) is laminated to the base layer. The elastomeric covering layer is stretched along direction (24) before lamination, such that at least the cuff portion is elastomerically biased to curl into a spiral. Windows (20) are defined in the elastomeric portion to provide for electrical conduction between the electrodes (12) and nerve tissue about which the cuff electrode is wrapped. The electrodes are arced (FIG. 6) such that they are more recessed adjacent sides of the window than adjacent the center in order to provide a substantially uniform flux density across the electrode surface.

14 Claims, 4 Drawing Sheets

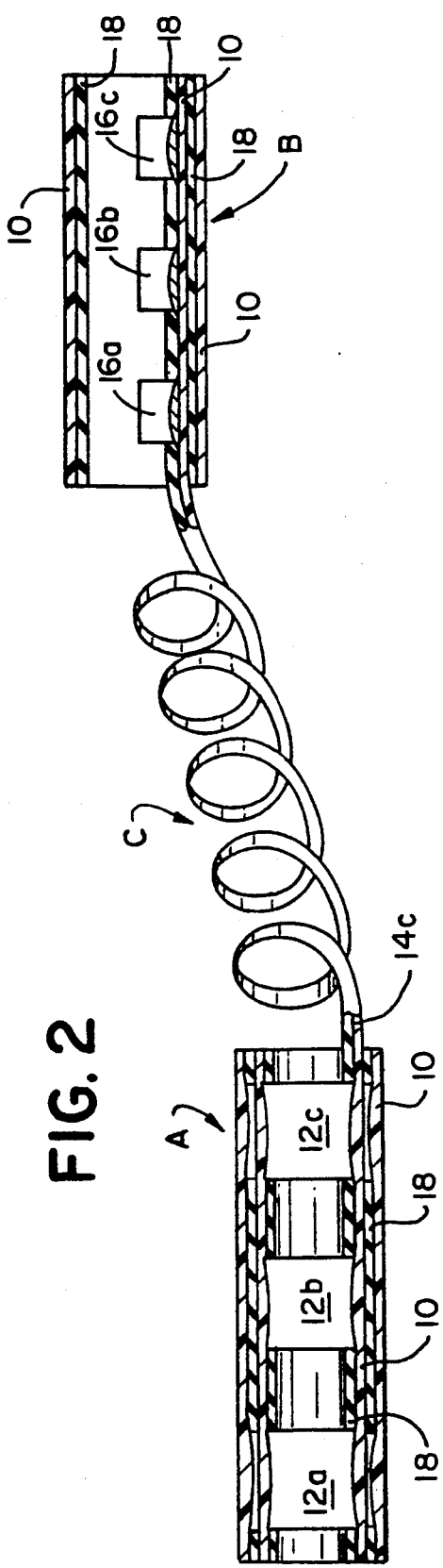
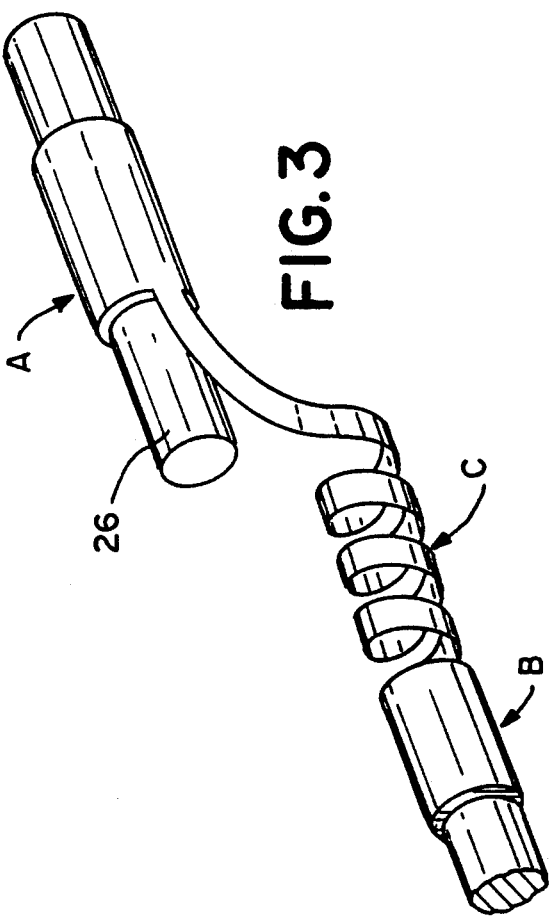
FIG. 2
FIG. 3
FIG. 4

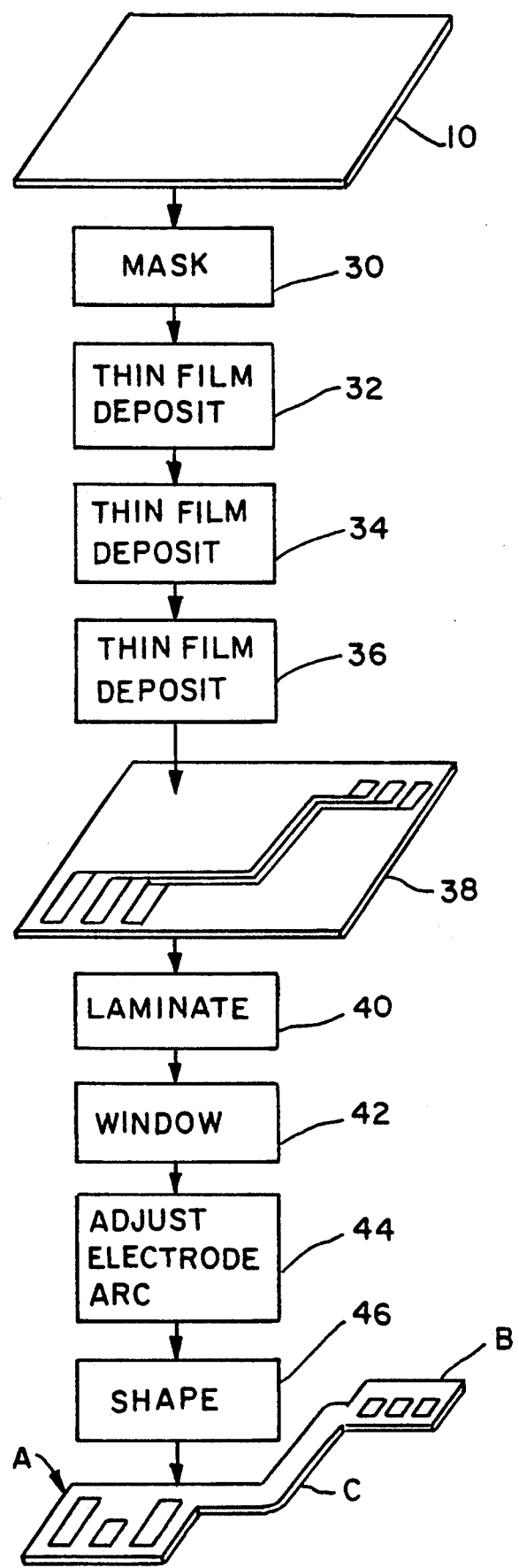

THIN FILM IMPLANTABLE ELECTRODE AND METHOD OF MANUFACTURE

BACKGROUND OF THE INVENTION

The present invention relates to the biomedical arts, particularly implantable electrodes. The present invention finds particular application in conjunction with cuff electrodes which are self-biased to curl around and snugly engage a nerve trunk, and will be described with particular reference thereto. It is to be appreciated, however, that the invention is also applicable to other types of implanted electrodes and biomedical devices.

Many types of nerve tissue damage do not heal. Such injuries leave a patient permanently without an appropriate nerve path for electrical signals or action potentials which travel from the brain to muscles or other biological tissue to cause a biological response. Similarly, such a discontinuity prevents action potentials from carrying sensory information or other biological feedback from the tissues to the brain. Moreover, there is also a tendency for action potentials to commence propagating naturally from below the injury site to the biological tissue causing an unconscious and unwanted biological response. Analogously, action potentials can propagate from above the injury site to the brain causing pain and erroneous sensory feedback.

Electrical potentials can be applied to nerve trunks and fibers to block the propagation of action potentials and for controllably initiating the propagation of action potentials in an upstream direction, a downstream direction, or both. Cuff electrodes, such as illustrated in U.S. Pat. No. 4,602,624 to Naples, Sweeney, and Mortimer controllably initiate and/or block action potentials in the nerves. Such cuff electrodes are self-biased to wrap around a nerve trunk in a spiral providing close contact. Because the electrode can be opened flat, it is surgically installed around the nerve fiber without cutting or damaging the nerve.

Although these prior art cuff electrodes have proven effective, they do have drawbacks. Primarily, the prior art cuff electrodes are labor intensive to manufacture. Metal foil strips are mounted and adhered to an elastomeric sheet. A second elastomeric sheet is stretched and laminated to the first elastomeric sheet. Apertures are provided in the second, stretched sheet to provide communication with the foil electrodes. Electrical leads are spot welded to the foil electrodes.

Interconnecting the leads with the electrodes at the cuff has drawbacks. First, the interconnection tends to increase the bulk of the electrode. Second, a failure of the spot weld requires removal of the electrode and the implantation of a new electrode.

Another drawback is that flat and annular sheet surface electrodes do not provide a uniform current density across their entire face. Rather, there tends to be a higher current flux adjacent the edges causing more rapid electrolytic degradation of the electrode edges. This concentration of the electrical flux at the edges accelerates edge degradation and corrosively reduces the size of the electrode. The size reduction, in turn, changes the electrical properties of the electrode.

The present invention provides a new and improved cuff electrode and method of manufacture which overcomes the above-referenced problems and others.

SUMMARY OF THE INVENTION

In accordance with the present invention, electrodes and conductors are applied to a polymeric sheet by thin film deposition.

In accordance with a more limited aspect of the present invention, a sheet of elastomeric material is stretched and adhered to the polymeric sheet to form a laminate which is self-biased to curl into a spiral. Apertures are provided in the elastomeric sheet overlaying the thin film electrodes. The apertures may be provided either before the elastomeric sheet is laminated to the polymeric sheet or after the lamination.

In accordance with a more limited aspect of the present invention, the thin film deposition process includes at least one of physical vapor deposition, chemical vapor deposition, and sputtering.

In accordance with a more limited aspect of the present invention, the electrode deposition step includes depositing successive layers of titanium, platinum, titanium and materials such as iridium that exhibit supercapacitor like properties.

In accordance with another more limited aspect of the present invention, portions of the titanium layer are selectively oxidized to form an insulative coating.

In accordance with another aspect of the present invention, the polymeric sheet includes a generally rectangular cuff portion on which the electrode films are deposited; an electrical connection portion displaced therefrom; and an elongated electrical lead portion extends between the cuff portion and the connection portion. The thin film deposition step further includes depositing thin film electrical leads from each thin film electrode along the electrical lead portion to the electrical connection portion and defining enlarged electrical contacts on the electrical contact portion.

In accordance with another aspect of the present invention, the thin film electrode surfaces are arced, such that a central portion is closer to the nerve tissue and an edge portion is more displaced from the nerve tissue. The arc is selected such that the current flux from the electrode to the nerve is substantially uniform across the electrode.

In accordance with another aspect of the present invention, an improved cuff electrode is provided. The electrode includes an electrode cuff portion having conductive electrode surfaces defined thereon. The electrode cuff portion is self-biased to curl into a spiral. An electrical contact portion is displaced from the cuff portion. An elongated lead portion interconnects the cuff and contact portion. Continuous electrically conductive layers each define an electrical contact surface on the cuff portion, an electrical contact surface on the connection portion, and a continuous lead therebetween across the electrical lead portion.

In accordance with another aspect of the present invention, a cuff electrode is provided in which electrical contact surfaces are defined between a polymeric layer and a stretched elastomeric layer, which elastomeric layer has apertures overlying the electrode surfaces. The elastomeric portion is stretched such that the cuff electrode is self-biased to curl in a spiral with the electrode surfaces facing an interior thereof.

In accordance with another aspect of the present invention, an electrode is provided having a non-conductive base portion and a conductive electrode portion. The electrode portion is arced to be more recessed at its edge regions such that a substantially uniform current density flows from all portions of the electrode surface into surrounding tissue.

In accordance with a more limited aspect of the arced electrode surface invention, the electrode surface is recessed in a shallow well.

One advantage of the present invention is that it reduces manual labor and manufacturing time.

Another advantage of the present invention is that it facilitates automated, mass production techniques.

Another advantage of the present invention is that it facilitates implantation and interconnection with electrical leads.

Another advantage of the present invention is that it prolongs electrode life.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

FIG. 2 is a view of the electrode construction of FIG. 1 in its curled spiral configuration in partial section;

FIG. 3 is a perspective view of the electrode construction with the cuff portion wrapped about a nerve trunk and the contact portion wrapped around the end of an electrical lead;

FIG. 4 is a section view transversely through FIG. 3;

FIG. 7 is a diagrammatic illustration of a preferred and alternate methods for constructing the cuff electrode.

DETAILED DESCRIPTION OF THE PREFERRED EMBODIMENTS

Figure 1:
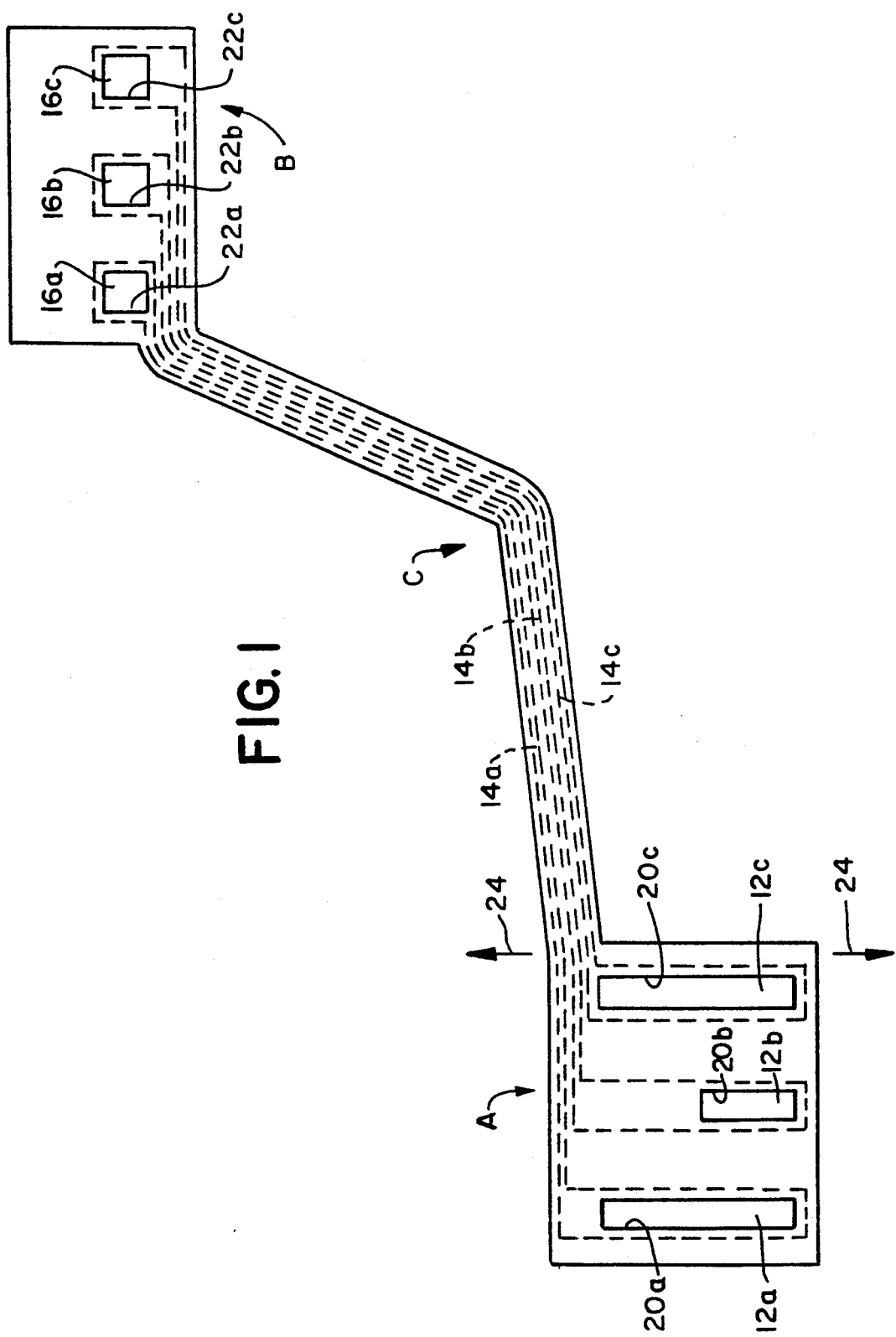
FIG. 1 is a top view of an electrode construction in accordance with the present invention with the cuff portion held flat.

With reference to FIGS. 1 and 2, the cuff electrode includes a cuff portion A and a connection portion B which are interconnected by a lead portion C. A polymeric layer 10 forms a base for the cuff, connection, and lead portions. A plurality of thin film electrodes 12a, 12b, and 12c are defined thin film material. Thin film electrical leads 14a, 14b, and 14c are integrally connected with the electrode paths and extend along the interconnecting lead portion C to the connection portion B. Contact pads or regions 16a, 16b, and 16c are formed on the lower substrate 10 and each interconnected with a corresponding one of the thin film leads.

An elastomeric covering 18 is laminated to the base layer 10 and thin film portions. The elastomeric material defines windows 20a, 20b, and 20c to provide electrical access to each of the thin film electrodes 12a, 12b, and 12c, respectively. The elastomeric layer further defines apertures 22a, 22b, and 22c to expose the contact pads 16a, 16b, and 16c respectively. The elastomeric layer 18 is stretched along a direction 24 prior to lamination.

With reference to FIGS. 3 and 4, when the covering layer 18 is contracted, particularly allowed to relax, it biases the cuff portion into a spiral. The firmness with which the cuff portion curls into a spiral, hence presses against an encircled nerve 26, is controlled by the resiliency of the elastomeric layer and the degree of stretching along the circumferential direction. The covering layer may also be stretched along the lead section C or the connection pad B to bias these regions to curl. Alternately, the covering layer may be a material which can be caused to contract in a selected direction, such as by heat, chemical reaction, physical stress, electrical stimulation, and the like. An insulating material other than the elastomeric layer may cover the film electrical leads C, any insulated portions of the contact pads 16, any insulated portions of the electrodes 12.

Figure 5:
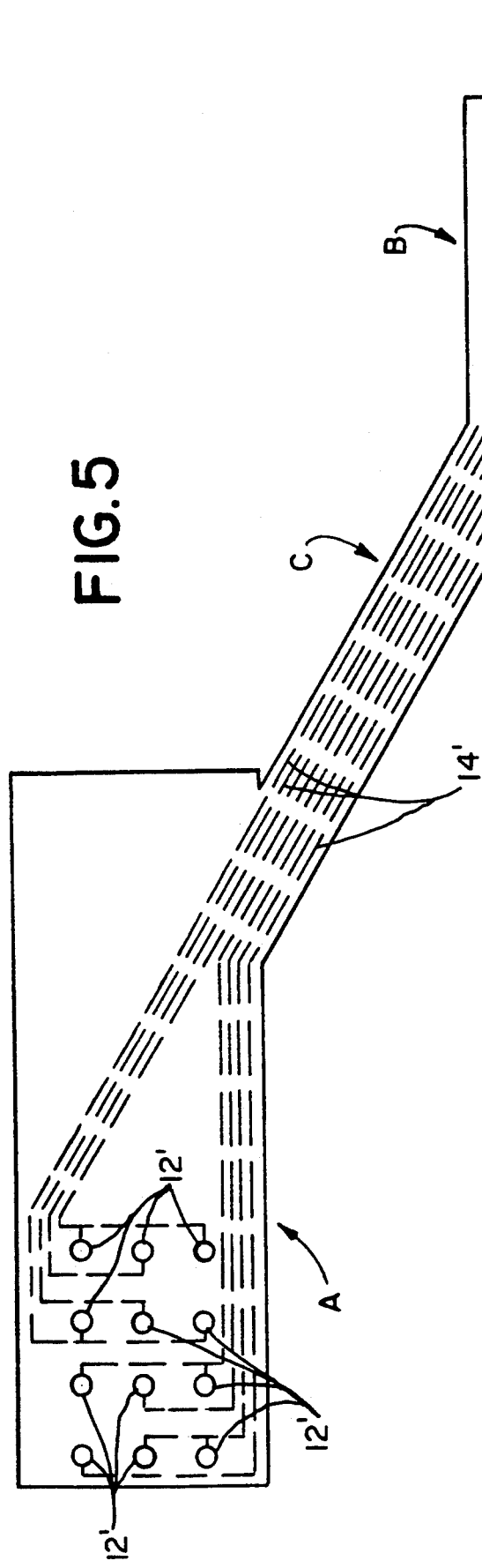
FIG. 5 is an alternate embodiment of an electrode construction in accordance with the present invention.
Figure 6:
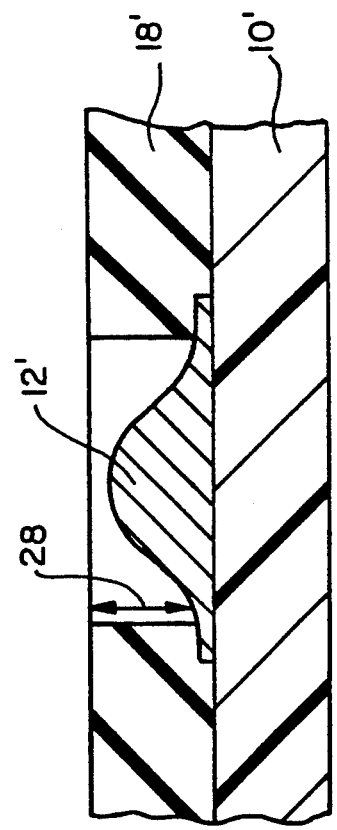
FIG. 6 is a detailed, cross-sectional view of the electrode surfaces of FIGS. 1 and 2, enlarged, and with exaggerated curvature to illustrate arcing of the electrode surface for uniform current distribution.

With reference to FIGS. 5 and 6, other configurations are also contemplated. For example, fewer or more electrodes may be incorporated into the cuff, as may be appropriate for the electrical stimulus to be applied. For example, for arced surfaces, the electrode pattern includes several sets of dot or circular electrodes 12'. The electrodes 12', electrical lead lines 14', and contact pads 16' are defined on a polymeric layer 10'. A stretched layer 18' is applied over leads and selected portions of the electrodes and contact pads.

With reference to FIG. 6, there tends to be a greater density of current flow from adjacent the edges of the electrode film 12' than adjacent the center, when the electrode film is flat and parallel to the surface. Recessing the electrode in a well caused by a height 28 of the inner coating 18' reduces the edge effects and improves current uniformity across the electrode. However, the covering layer 18' is relatively thin and the well is relatively shallow. To improve linearity, the electrode surface 12' is arced such that it is more recessed from the nerve contacting surface adjacent the edges than at the center. The exact arc shape is determined by the depth 28, the width of the electrode, and the like. The arc for a circular or other simple shaped electrode is amenable to calculation. However, in the preferred embodiment, it is determined empirically. More specifically, a relatively thick, flat electrode is disposed at the bottom of a well of the dimension and depth of each electrode well. The completed electrode structure is placed in an electrolytic solution including the proper buffers and additives to perform an electroplating type operation. A sufficient current is applied to the electrode such that material is electrolytically removed from the electrode and carried into the solution. As the electrochemical etching or electroplating procedure is continued, more material is removed from the electrode in the areas with the highest current density, and less in the areas with lowest current density. This process is continued until a substantially uniform current flux across the electrode is achieved. After such substantially uniform current flux is achieved, the curvature is measured. The measured arc is defined in subsequent electrodes of the same size and depth.

With reference to FIG. 7, a mask which defines the electrodes, leads, and connection points, such as the pattern illustrated in phantom in FIG. 1 or FIG. 5 above, is applied over the base sheet 10 in a masking step 30. In a thin film deposition step 32, a thin film of electrically conductive atoms is deposited through the mask. In the preferred embodiment, the first thin film deposition step impregnates a coat of titanium atoms about 200–500 angstroms thick. For example, the titanium can be deposited by sputtering, chemical vapor deposition, physical vapor deposition, or the like and driven into polymeric layer 10 by bombardment with an inert plasma beam of argon or the like. Other techniques such as ion implantation can also be used to embed a sufficient number of titanium atoms into the polymeric material so as to form a base which will remain adhered when the polymeric material is flexed or stretched.

In a second thin film deposition step 34 a layer of iridium of about 100–20,000 angstroms is deposited through the mask onto the titanium film. Platinum, rhodium, palladium, nickel, copper, gold, tantalum alloys thereof, stainless steel, and other conductive, relatively inert, corrosion resistant metals are also contemplated.

Optionally, a third deposition step 36 may be performed to deposit a second layer of titanium or other metals such as those listed above, through the mask on top of the second layer. The titanium layer is advantageous in that the titanium is readily oxidized to form an insulator. The titanium can be oxidized to shape the electrodes, to insulate the leads and portions of the contact pads from surrounding tissue, to provide a thin insulative layer between the electrodes and the tissue for a capacitive electrode coupling, and the like. The titanium can also be partially oxidized adjacent to the edges of the electrode. As discussed above, there tends to be a greater current flux density adjacent to the edge portions of the electrode than across the center. The edge portions can be selectively oxidized such that the current flux between the electrode and the tissue is substantially uniform across the electrode.

The arc in the electrode surface is formed in the deposition step. More specifically, masks of progressively smaller dimensions are used or a smaller mask dithered such that the deposition thickness is thicker in the center than at the edges. Alternately, a combination of shaping of base layer 10 and adjusting the thickness of the electrode surface may be used.

The mask is removed to provide a partially finished workpiece 38 with the electrically conductive electrodes, connection paths, and leads defined on a surface of the base sheet 10. Alternately, a complete conductive layer can be deposited in the depositing steps and the completed layer etched through a mask to define the electrode, lead, and contact pad pattern.

In a covering step 40, the partially completed workpiece 38 is covered with an elastomeric material in a stretched or elongated state at least along the circumferential axis 24 of the cuff portion A. The coating step is selectively performed by stretching a sheet of silicon rubber and adhesively bonding it to the base 10, the leads, and portions of the electrodes and the contact pads which are to be insulated from surrounding tissue. Of course, other means can be used to create a local stress in the layer that provides the curling action either by tension on the inner layer or compression on the outer layer. For example, a layer of a heat shrink polymer may be bonded to the base layer 10. The electrode assembly may be heated sufficiently to cause a differential contraction of the base layer and the coating layer such that the electrode is biased into a spiral.

Preferably, the coating sheet is stretched and contracted along the connection pad B or the lead portion C such that these portions also curl. Alternately, the coating may be stretched to a lesser degree along the lead or connection portion to provide limited curling and resiliency.

In a window defining step 42, the windows 20 and 22 are defined in the elastomeric layer 18. In the preferred embodiment, the window defining step 42 is performed after the coating step to cut and remove the windows from the laminated construction. Alternately, the window defining step may be performed prior to the coating step. For example, the elastomeric layer can be die cut, including the windows, before it is stretched and laminated to the base layer. As yet another alternative, the windows may be defined by rendering those portions of the covering layer 18 electrically conductive, such as by metal ion implantation, chemical doping, or the like.

After the windows are formed in the electrodes, the curvature of the electrode surface is adjusted with a curvature adjusting step 44. In the curvature adjusting step, the completed electrode is immersed in an electrolytic solution as described above and a current applied such that a surface layer of the electrode is electrolytically etched, generally in proportion to current density perfecting the curvature and polishing the surface. Typically, the center of the electrode is raised above the edge of the electrode, i.e. less recessed into the well, by about 20% of the radius (or minor dimension) of the electrode.

In a shaping step 46. the sheet is shaped to define the cuff portion A, the connecting portion B, and the lead portion C. Various shaping techniques are contemplated such as die cutting, molding, trimming, and the like. Moreover, the shaping step can be performed at various points in the process from the first step through the last.

In alternate embodiments, the base layer begins as a fluid that is cured to form the base layer 10. The fluid is poured on a rigid substrate, which preferably defines an outline of the cuff electrode assembly. The cover layer can be formed analogously from a liquid. The rigid substrate functions as a carrier during the curing, the formation of the electrodes, the application of the cover layer, and other steps of the process. The completed cuff electrode assembly is peeled from the rigid substrate. As another alternative, one or more additional cuff portions may be connected by additional lead portions with the same connection region B, preferably defined on the common base layer 10.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A method of manufacturing a cuff electrode comprising:

vapor depositing a thin electrically conductive film which defines electrodes, electrical leads, and electrical contacts on a surface of a flexible, insulating base sheet;

laminating a cover layer to the surface of the base sheet and at least portions of the electrically conductive film;

shaping the base sheet to define a cuff portion containing the electrodes, an electrical contact portion displaced from the cuff portion, the electrical contact portion containing the electrical contacts, and a thin, elongated flexible electrical lead portion connected between the cuff and electrical contact portions and containing at least part of the electrical leads;

contracting the cover layer such that the cover layer, the base sheet, and the electrically conductive film curl into a spiral.

2. The method as set forth in claim 1 further including defining windows through the cover layer in communication with at least portions of the electrodes to provide an electrically conductive path between the electrode and an interior of the spiral.

3. The method as set forth in claim 1 wherein the covering layer is an elastomeric material and wherein in the covering layer laminating step, the elastomeric material is stretched along a first direction and laminated to the cuff portion, the electrical lead portion, and the electrical contact portion, such that the cuff, lead, and contact portions curl into spirals as the covering layer contracts.

4. The method as set forth in claim 1 wherein the base sheet is a polymeric material.

5. The method as set forth in claim 1 further including contouring the electrodes such that the electrodes are arced and are more raised centrally and more recessed adjacent peripheral edges.

6. A method of manufacturing a cuff electrode comprising:

impregnating electrode and lead regions of a polymeric sheet with a first metal;

depositing a thin film of a second metal on the first metal impregnated electrode and lead regions of the polymeric sheet;

covering at least regions of the polymeric sheet surrounding the electrode regions with a cover layer;

contracting the cover layer such that the cover layer, the polymeric sheet, and the second metal film curl into a spiral.

7. The method as set forth in claim 6 wherein the first metal is titanium and the second metal is one of platinum, iridium, rhodium, palladium, nickel, gold, copper, and alloys thereof.

8. A method of manufacturing an electrode comprising:

on a flexible base layer defining an enlarged cuff portion, an enlarged electrical contact portion, and a narrow, elongated lead portion extending therebetween;

positioning a mask adjacent the base layer which mask defines electrodes on the cuff portion, contact pads on the contact portion, and electrical leads extending between the electrodes and contact pads along the elongated lead portion;

thin film vapor depositing electrodes, leads, and contact pads through the mask onto the base layer;

laminating a covering layer to at least the lead portion; and, contracting the covering layer along a selected direction such that the lead portion curls into a spiral.

9. The method as set forth in claim 8 further including forming the electrode such that the electrode is arced and more recessed adjacent its edges.

10. A cuff electrode, comprising:

a base layer defining a cuff portion, an electrical connection portion displaced from the cuff portion, and an elongated electrical lead portion extending between the cuff and electrical connection portions;

a plurality of electrode surfaces deposited on the cuff portion;

a plurality of electrical contact pads defined on the connection portion;

a plurality of electrical leads deposited in electrical communication between the electrode surfaces on the cuff portion and the connection pads on the electrical contact portion, the electrical leads being deposited along the electrical lead portion;

a covering layer laminated to at least the lead portion, the covering layer being contracted along a first direction such that the lead portion curls in a spiral.

11. The electrode as set forth in claim 10 wherein the covering layer covers the cuff portion and defines a window in conjunction with each electrode surface such that an electrically conductive path is defined to each electrode surface.

12. The electrode as set forth in claim 10 wherein the electrode surfaces, leads, and contact pads are vapor deposited thin films.

13. The electrode as set forth in claim 11 wherein the electrode surfaces are arced such that the electrodes are more recessed adjacent edges of the windows than adjacent a central portion of the windows.

14. A cuff electrode comprising:

a polymeric base layer defining a cuff including a plurality of electrode regions, a plurality of electrical connection regions, a plurality of elongated electrical lead regions extending between the electrode regions and the electrical connection regions, the electrode regions, the electrical connection regions, and the electrical lead regions being impregnated with first metal ions;

thin film electrodes deposited on the metal ion impregnated electrode regions of the base layer;

thin film electrical leads deposited on the metal ion impregnated electrical lead regions;

thin film electrical connection surfaces deposited on the metal ion impregnated electrical connection regions;

a covering layer which covers at least the thin film electrical leads and non-electrode regions of the base layer, the covering layer being contracted along a first direction such that the base layer, thin film electrodes, and covering layer are resiliently biased to curl into a spiral.

* * * * *